(12) United States Patent
Stauber

(10) Patent No.: US 10,792,076 B2
(45) Date of Patent: Oct. 6, 2020

(54) SPINE SURGERY DEVICE AND METHOD

(71) Applicant: GLOBUS MEDICAL, INC., Audubon, PA (US)

(72) Inventor: Marshall E. Stauber, Hollywood, FL (US)

(73) Assignee: Globus Medical, Inc., Audubon, PA (US)

( * ) Notice: Subject to any disclaimer, the term of this patent is extended or adjusted under 35 U.S.C. 154(b) by 0 days.

(21) Appl. No.: 16/222,428

(22) Filed: Dec. 17, 2018

(65) Prior Publication Data
US 2019/0125414 A1 May 2, 2019

Related U.S. Application Data

(63) Continuation of application No. 14/933,091, filed on Nov. 5, 2015, now Pat. No. 10,182,850, which is a continuation of application No. 12/556,367, filed on Sep. 9, 2009, now Pat. No. 9,211,144.

(51) Int. Cl.
*A61B 17/70* (2006.01)
*A61B 17/88* (2006.01)

(52) U.S. Cl.
CPC ...... *A61B 17/7052* (2013.01); *A61B 17/7049* (2013.01); *A61B 17/8869* (2013.01)

(58) Field of Classification Search
CPC ............ A61B 17/7001; A61B 17/7005; A61B 17/7007; A61B 17/7008; A61B 17/7022–7032; A61B 17/7049–7052; A61B 17/7056; A61B 17/8869; A61B 17/70
See application file for complete search history.

(56) References Cited

U.S. PATENT DOCUMENTS

| | | | | |
|---|---|---|---|---|
| 5,380,325 A | * | 1/1995 | Lahille | A61B 17/7041 606/250 |
| 5,487,742 A | * | 1/1996 | Cotrel | A61B 17/7052 606/250 |
| 5,522,816 A | | 6/1996 | Dinello et al. | |
| 5,743,911 A | * | 4/1998 | Cotrel | A61B 17/7049 606/246 |
| 5,928,231 A | * | 7/1999 | Klein | A61B 17/823 606/218 |
| 5,989,251 A | * | 11/1999 | Nichols | A61B 17/7049 606/246 |
| 6,352,537 B1 | * | 3/2002 | Strnad | A61B 17/7007 606/276 |
| 6,589,243 B1 | * | 7/2003 | Viart | A61B 17/7047 606/250 |
| 6,786,907 B2 | | 9/2004 | Lange | |
| 8,262,700 B2 | * | 9/2012 | Cho | A61B 17/7049 606/250 |
| 8,465,526 B2 | * | 6/2013 | Friedrich | A61B 17/7007 606/257 |
| 8,926,673 B2 | * | 1/2015 | Clement | A61B 17/7001 606/276 |

(Continued)

*Primary Examiner* — Eduardo C Robert
*Assistant Examiner* — Michelle C Eckman

(57) ABSTRACT

A surgical connector useful to link spine rods together. The connector may be used adjacent a pair of mounting screws in one vertebra to limit movement between the screws or may be used to apply a lateral force to a portion of the spine to change curvature. A method of performing spinal surgery is also provided to reinforce a patient's spine.

20 Claims, 2 Drawing Sheets

(56) References Cited

U.S. PATENT DOCUMENTS

| | | | |
|---|---|---|---|
| 9,055,979 B2* | 6/2015 | Alcock | A61B 17/7008 |
| 9,101,403 B2* | 8/2015 | Biedermann | A61B 17/7037 |
| RE47,377 E* | 5/2019 | Rice | A61B 17/7085 |
| 10,420,590 B2* | 9/2019 | Le Couedic | A61B 17/7053 |
| 2002/0143327 A1* | 10/2002 | Shluzas | A61B 17/7049 |
| | | | 606/252 |
| 2005/0080416 A1* | 4/2005 | Ryan | A61B 17/7049 |
| | | | 606/252 |
| 2005/0107788 A1 | 5/2005 | Beaurain et al. | |
| 2005/0113831 A1* | 5/2005 | Franck | A61B 17/7052 |
| | | | 606/250 |
| 2005/0149019 A1* | 7/2005 | Sasing | A61B 17/7049 |
| | | | 606/250 |
| 2005/0203513 A1* | 9/2005 | Jahng | A61B 17/1757 |
| | | | 606/254 |
| 2005/0261686 A1* | 11/2005 | Paul | A61B 17/7023 |
| | | | 606/254 |
| 2006/0041259 A1* | 2/2006 | Paul | A61B 17/7023 |
| | | | 606/250 |
| 2006/0064091 A1 | 3/2006 | Ludwig et al. | |
| 2006/0142758 A1 | 6/2006 | Petit | |
| 2006/0217718 A1 | 9/2006 | Chervitz et al. | |
| 2007/0083201 A1* | 4/2007 | Jones et al. | A61B 17/7049 |
| | | | 606/252 |
| 2007/0179501 A1* | 8/2007 | Firkins | A61B 17/705 |
| | | | 606/254 |
| 2007/0213723 A1* | 9/2007 | Markworth | A61B 17/7049 |
| | | | 606/914 |
| 2008/0039843 A1 | 2/2008 | Abdou | |
| 2008/0154306 A1* | 6/2008 | Heinz | A61B 17/7055 |
| | | | 606/256 |
| 2008/0161854 A1* | 7/2008 | Bae | A61B 17/7007 |
| | | | 606/246 |
| 2008/0161857 A1* | 7/2008 | Hestad | A61B 17/025 |
| | | | 606/264 |
| 2008/0172093 A1* | 7/2008 | Nilsson | A61B 17/7049 |
| | | | 606/250 |
| 2008/0262546 A1* | 10/2008 | Calvosa | A61B 17/7031 |
| | | | 606/250 |
| 2008/0262551 A1* | 10/2008 | Rice | A61B 17/7085 |
| | | | 606/268 |
| 2008/0294198 A1* | 11/2008 | Jackson | A61B 17/7008 |
| | | | 606/246 |
| 2008/0306539 A1 | 12/2008 | Cain et al. | |
| 2008/0306545 A1 | 12/2008 | Winslow et al. | |
| 2009/0082815 A1* | 3/2009 | Zylber | A61B 17/7008 |
| | | | 606/295 |
| 2009/0099606 A1* | 4/2009 | Hestad | A61B 17/7004 |
| | | | 606/254 |
| 2009/0131982 A1* | 5/2009 | Schwab | A61B 17/7001 |
| | | | 606/246 |
| 2009/0198281 A1* | 8/2009 | Rice | A61B 17/7031 |
| | | | 606/279 |
| 2009/0204150 A1* | 8/2009 | Hochschuler | A61B 17/7001 |
| | | | 606/246 |
| 2009/0299411 A1* | 12/2009 | Laskowitz | A61B 17/7008 |
| | | | 606/246 |
| 2011/0060367 A1* | 3/2011 | Stauber | A61B 17/7049 |
| | | | 606/250 |
| 2011/0071589 A1 | 3/2011 | Black | |
| 2011/0106185 A1* | 5/2011 | Gil | A61B 17/7022 |
| | | | 606/86 R |
| 2011/0184463 A1* | 7/2011 | Schwend | A61B 17/705 |
| | | | 606/258 |
| 2011/0245872 A1* | 10/2011 | Nilsson | A61B 17/7049 |
| | | | 606/250 |
| 2012/0158065 A1* | 6/2012 | Jouve | A61B 17/7001 |
| | | | 606/276 |
| 2013/0030467 A1* | 1/2013 | Karas | A61B 17/686 |
| | | | 606/248 |
| 2013/0030469 A1* | 1/2013 | Karas | A61B 17/1757 |
| | | | 606/264 |
| 2013/0030470 A1* | 1/2013 | Karas | A61B 17/1757 |
| | | | 606/264 |
| 2014/0148854 A1* | 5/2014 | Carlson | A61B 17/7049 |
| | | | 606/254 |
| 2015/0209084 A1* | 7/2015 | Roberto | A61B 17/7055 |
| | | | 606/250 |
| 2019/0269440 A1* | 9/2019 | Patrinicola | A61B 17/7052 |

* cited by examiner

SPINE SURGERY DEVICE AND METHOD

CROSS-REFERENCE TO RELATED APPLICATIONS

The present application is a continuation of U.S. patent application Ser. No. 14/933,091, filed Nov. 5, 2015, which is a continuation of U.S. patent application Ser. No. 12/556,367, filed Sep. 9, 2009, now U.S. Pat. No. 9,211,144, which are hereby incorporated by reference in their entireties for all purposes.

FIELD OF THE INVENTION

A device for use in spine surgery to extend between and connect rods used to reinforce portions of a spine. The device includes a cross connector used to connect rods secured to the spine on opposite sides of the spine. The device includes a flexible connector and a rigid connector that act together to limit bilateral movement between the rods.

BACKGROUND OF THE INVENTION

Spinal surgery can be performed through large incisions or percutaneously, i.e., through small incisions using instruments specifically designed to allow the performance of surgery through small incisions. Such procedures are well known. Percutaneous procedures are often preferred because they are less invasive and leave less external scar tissue. However, some procedures are difficult to perform percutaneously because of the configuration of the devices to be installed.

In the performance of spine surgery for such things as scoliosis, disc removal or replacement, spine fusion, bone grafts and spine deformity or weakness from cancer, metal (used to mean metal alloys and metal) rods are secured to the spine to help support the spine and/or straighten the spine. Rods may also be used to redistribute load on various vertebrae. Rods may be secured to the spine on opposite sides of the spine for extra support and rigidity.

For scoliosis, surgery is used primarily for severe cases or for curves that do not respond to bracing. Surgery has two main goals—to stop a curve from progressing and to correct spinal deformity.

There are various techniques used for scoliosis surgery. One type of surgery involves posterior spinal fusion with instrumentation and bone grafting. This surgery is performed through the patient's back while the patient lies on their stomach. During this type of surgery, the surgeon attaches a metal rod to each side of the patient's spine by using hooks or screws attached to the vertebral bodies. Then, the surgeon fuses the spine with a piece of bone from the patient's hip (a bone graft). The bone grows in between the vertebrae and holds them together and straight. This process is called spinal fusion. The metal rods attached to the spine ensure that the backbone remains straight while the spinal fusion takes place.

The only lateral support for the rods is the vertebral bodies to which the rods are attached and the rods themselves. Additionally, the only support for the screws installed in the bones to support the rods is the bones themselves and perhaps to some extent, the rods and adjacent screws on the same rod. In the treatment spinal curvature as in the treatment of scoliosis, the spine needs to be brought to a less laterally curved condition which is difficult to do in percutaneous surgery since very little of the length of the rods is exposed.

There is thus a need for an improved means to perform back surgery when rods are utilized.

SUMMARY

The present invention involves the provision of a cross connector for use in spine surgery such as percutaneous spine surgery. The cross connector includes first and second hooks each having a throat partially defined by a shank with the throats opening generally toward one another. The throats are adapted to receive a respective rod secured to a spine therein. A flexible connector is secured to the first hook and extends to the second hook. The second hook includes means to facilitate securement of the second hook to the flexible connector and fix the maximum separation between the first and second hooks. A rigid connector is secured to and extends between the first and second hooks to fix the distance of their separation.

The present invention also involves the provision of a method of conducting spinal surgery wherein rods are connected to opposite sides of the spine. The method includes providing access to the posterior of the spine on opposite sides thereof. First and second hooks are associated with first and second rods secured to a patient's spine in laterally spaced relationship. The first and second hooks are each associated with a respective said rod by tensioning a flexible connector associated with and extending between the hooks. A rigid connector is mounted to the first and second hooks to extend therebetween to fix the lateral spacing between the hooks.

BRIEF DESCRIPTION OF THE DRAWINGS

Like numbers used throughout this application represent like or similar parts and/or construction.

DETAILED DESCRIPTION OF THE INVENTION

Figure 1:
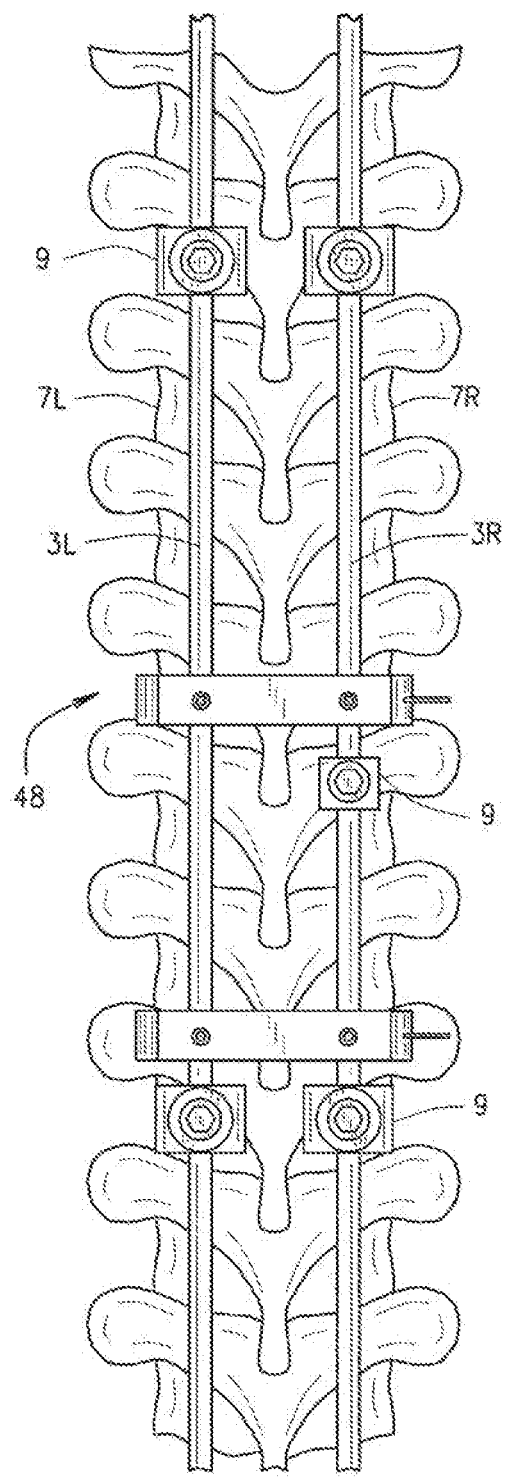
FIG. 1 is a rear elevation view of a spine with attached rods and a plurality of cross connectors.
Figure 4:
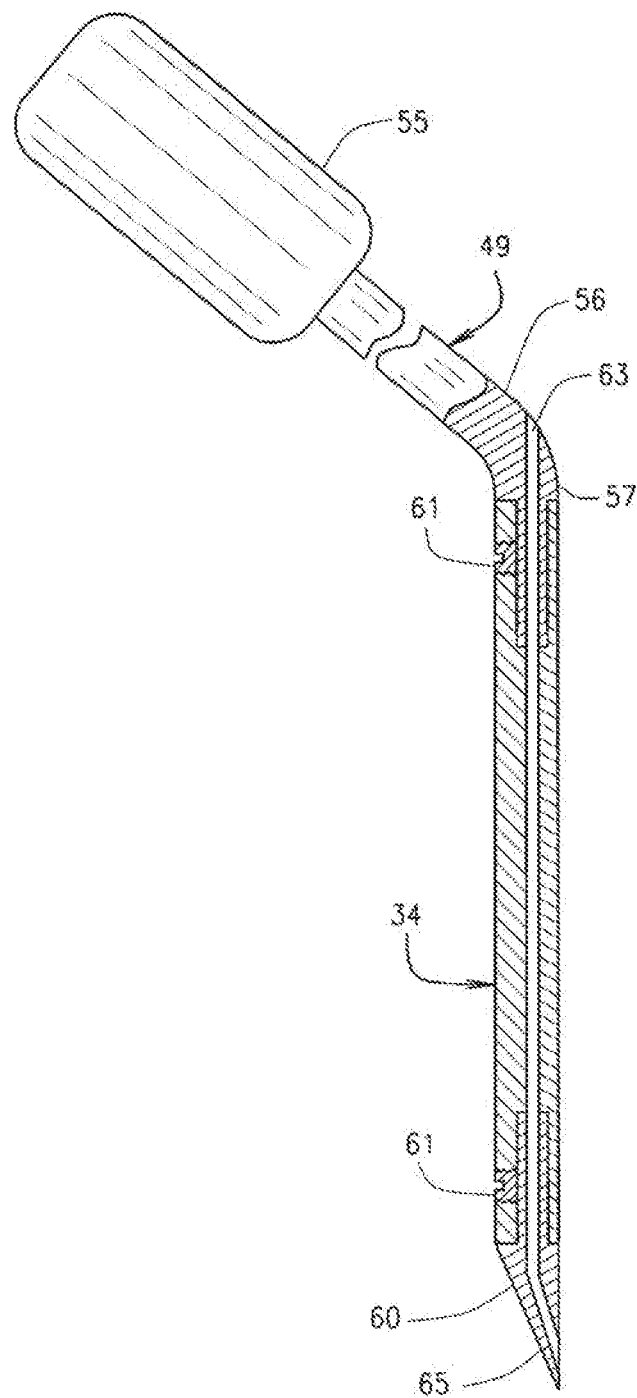
FIG. 4 is an elevation view of a tool usable in the installation of the cross connector.

While the present invention is susceptible of embodiment in various forms, there is shown in the drawings and will hereinafter be described presently preferred embodiments with the understanding that the present disclosure is to be considered an exemplification of the invention and is not intended to limit the invention to the specific embodiments illustrated.

The reference numeral 1 designates generally a cross connector for attachment to a pair of laterally spaced apart rods 3L, 3R (FIGS. 1, 3) secured to a spine 5 and positioned on opposite sides 7L, 7R of the spine. The rods 3 may be held in place via screw mounts 9 secured to a vertebra 10. Such screw mounts 9 are well known in the art. The rods 3 extend longitudinally between various vertebrae 10 and may be attached to alternate vertebrae 10A, 10C on alternate sides 7L, 7R. Two forms of mounting of the connector 1 are shown, one form where the connector 1 is mounted between the rods 3L, 3R adjacent screws 9 attached to one vertebra 10 and one form where the connector 1 is mounted between the rods 3L, 3R with one rod at that location being mounted to one vertebra while the other rod is free of mounting to that vertebra to assist in straightening the spine 5. That is, a rod 3 bridges one or more vertebrae without attachment thereto.

Figure 2:
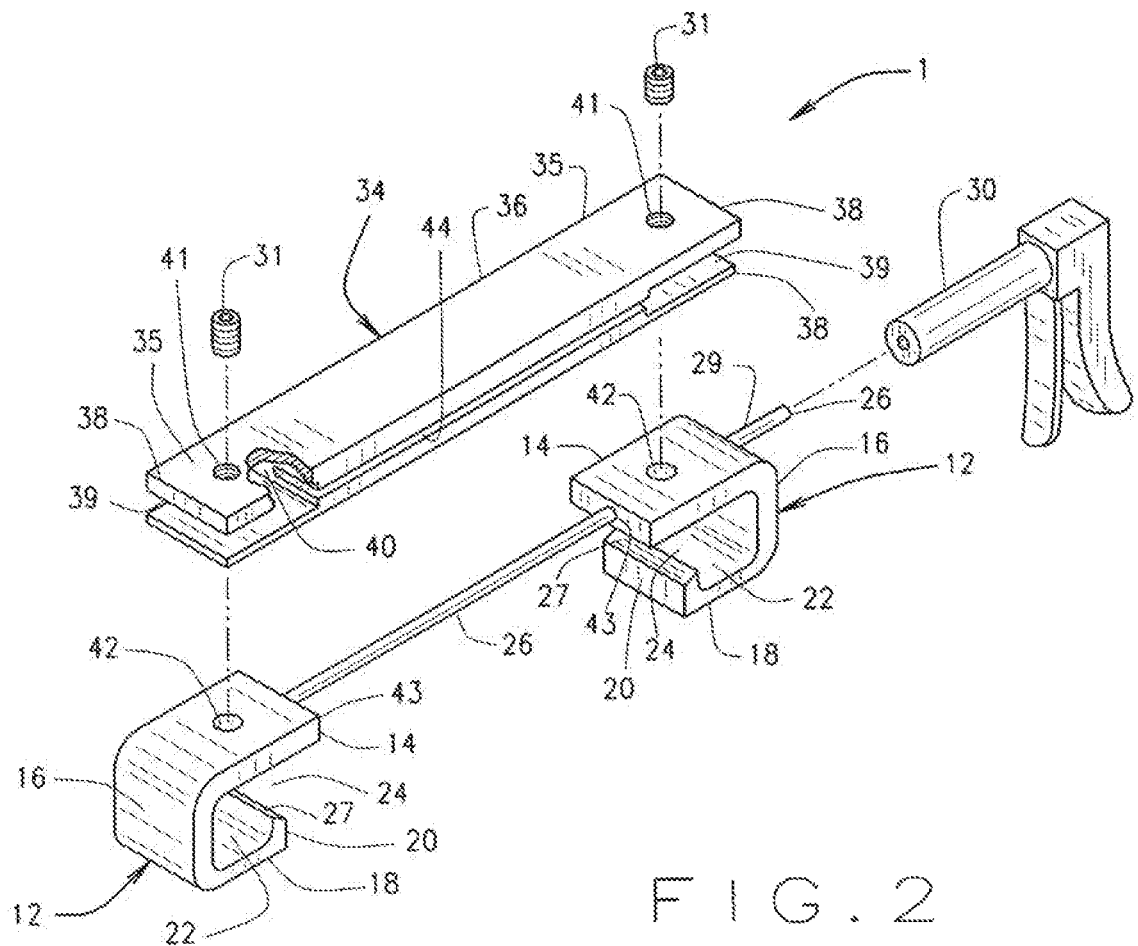
FIG. 2 is an enlarged perspective view of a cross connector as shown in FIG. 1.
Figure 3:
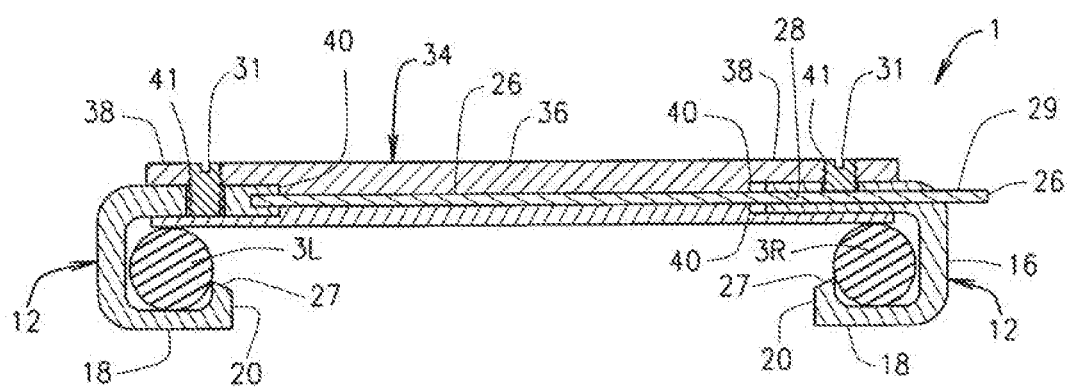
FIG. 3 is a sectional view of the cross connector of FIG. 2.

The connector 1, as best seen in FIGS. 2, 3, includes a pair of hooks 12. Preferably, the hooks 12 have substantially the same configuration and include a shank 14, a bight 16, a leg 18 and a latch 20 defining a throat 22 therebetween and a mouth 24 defined by the latch 20 and the shank 14. As configured for use, the throats 22 of the hooks 12 open generally toward one another. Preferably the hooks 12 are made of a metal and their component parts are integral. One hook 12 is shown as having an attached flexible connector 26 such as a multi strand metal cable on the order of ⅛ inch in diameter or smaller. As shown, the connector 26 is secured to a shank 14 and in use extends to the other hook 12 of a pair of hooks for securement thereto to effect mounting of the hooks each to a respective rod 3 by having a rod 3 positioned in a respective throat 22 after moving through a respective mouth 24. The hooks 12 and the connector hook 26 form a connector hook assembly with flexible link when assembled. In a preferred embodiment, the hooks 12 have a generally rectangular transverse cross sectional shape particularly in the shank 14. The edges and corners of a hook 12 (and other components of the connector 1) are preferably rounded. The latches 20 may also be provided with inclined surfaces 27 to facilitate mounting to a rod 3.

One of the shanks 14 of a pair of hooks 12 is configured to be associated with the flexible connector 26 to form an attached hook assembly. As shown, the shank 14 of one hook 12 is provided with a through passage 28 extending along a portion of the length of the shank 14. The flexible connector 26 is inserted into the passage 28 and has a free end portion 29 extend beyond the shank 14 for gripping by a tool 30 adapted to induce tension in the flexible connector 26 to effect attachment of the hook assembly to the rods 3. When the appropriate amount of tension is in the connector 26, the connector 26 and the hooks 12 are secured together to make an assembly as with a fastener 31 as described below. This attachment fixes the maximum spacing between the hooks 12 during use. Other means of attaching the free end portion 29 of the connector 26 may be utilized.

A rigid connector 34 is associated with the hook assembly and is operable to fix the hooks 12 against moving toward and away from one another and for tensile loading, it is redundant to the flexible connector 26. The connector 34 can resist both tensile and compression axial loading while the connector 26 can resist axial tensile loading. The connector 34 can be loaded in tension to resist hook separation or divergence and in compression to resist convergence toward one another. As shown, the connector 34 has opposite end portions 35 for connection to the shanks 14 of hooks 12 and a central rigid load bearing portion 36 extending between the hooks 12. Each of the end portions 35 includes a pair of longitudinally extending fingers 38 with a channel 39 therebetween. The shank 14 of a hook 12 is received in a respective channel 39 and is sandwiched between the fingers 38. As shown, the finger 38 in the throat 22 is positioned between a rod 3 and a shank 14 to lock it against bending. The outer fingers 38 overlie a respective shank 14 and can be used to secure the connector 34 to the shanks 14. As shown, a fastener 31, such as a set screw or a hex head screw may be threadably engaged in holes 41 and received in recesses 42 in the shanks 14. In the hook 12 with the passage 28 containing the connector 26, the fastener 31 may be used to engage the connector 26 to secure it to the hook 12. The connectors 34 can be provided in various lengths to accommodate different spacings between rods 3. Shoulders 40 are provided in the channels 39 to abut the ends 43 of the hooks 12 to help resist movement of one hook 12 toward the other hook 12 when the connector 1 is assembled and installed.

The connector 34 is also provided with means to allow the flexible connector 26 to extend between the hooks 12 preferably in a generally straight line. In the illustrated embodiment, an open sided groove 44 is positioned on the side of the central portion 36 and opens into each of the channels 39. This allows for the mounting of the connector 34 to the assembly of hooks 12.

The mouth 24 has an opening size less than the cross sectional dimension of the throat 22 and preferably less that the diameter of a rod 3 plus the thickness of a finger 38 to be received therein so the hook 12 can lock onto a rod 3 after mounting on a rod. The latch 20 and leg 18 are preferably resiliently deformable to form a resiliently deformable lock. The channels 39 and the hook shanks 14 are configured to resist rotational movement of the shanks 14 on the connector 34.

The present invention is better understood by a description of the use of the cross connector 1. A patient has rods 3 mounted to a spine 5 in laterally spaced relationship on opposite sides 7L, 7R of the spine. The rods 3 may have been previously installed or installed as part of the current procedure. Preferably, the procedure for installing the connector 1 is done percutaneously. Openings are formed on opposite sides of the spine 5 and a cannula or the like is inserted into each of the openings to provide access to surgical site. After rod installation, the rigid connector 34, the flexible connector 26 with hook 12 and the unattached hook 12 may be moved into place through an opening on one side under the skin to bridge the spine for attachment to the rods 3. As shown, the connector 1 may be mounted adjacent two rod mount screws 9 on one vertebra as at 48 or where there is a screw 9 for one rod in a vertebra and not the other rod so tension in the flexible connector 26 can either move a portion of the spine laterally or retain it in a less curved condition. An opening in the skin of the patient is made to provide access to the spine 5 and the rods 3 when installed. A hook 12 with the attached connector 26 is positioned in the surgery site and the connector 26 has its free end portion 29 exposed for access. The hook 12 is placed on a rod 3. The rigid connector 34 is then moved into place with an installation tool 49 and the flexible connector 26 is positioned in the groove 44 and the shank 14 of the inserted hook 12 is positioned in its respective channel 39 at which time, the fastener 31 may be installed to couple the connectors 26, 34 together. The tool 49 has a handle 55 and a shank 56 connected thereto. An end portion 57 is configured to have a connector 34 removably mounted thereon as with a cable 63 and threaded fastener 61. A foot 60 is removably mounted to the connector 34 and the cable 63 as with a fastener 61. The foot 60 may be provided with a tapered lead-in section 65. The free hook 12 has the connector 26 inserted through the passage 28 with the free end portion 29 being exposed for attachment to a tensioning tool 30. Such a tool can function like a pop rivet tool or a cable tie tightener. The tool 30 tensions the connector 26 and pulls the hooks 12 together. The connector 34 has its fingers 38 guided over the shanks 14 with the shanks each moving into a respective channel 39 if not already there. Tensioning the connector 26 also urges the rods 3 to each move through a respective mouth deforming a respective latch 20 to move into a respective throat. The rods 3 may each already be positioned in a respective throat 22 and a finger 38 may move into the throat 22 to lock the rod 3 in a respective throat. When the appropriate tension is reached, the holes 41 are properly aligned each with a respective recess 42 and the shoulders 40 abut the ends 43 of the shanks 14, the fasteners 31 may be installed and tightened to secure the connector 1 as an assembly and to retain tension in the connector 26 if desired. The free end portion 29 of connector 26 may cut off if desired. When installed, the connector 1 can maintain a spine's lateral curvature and can also be used to reinforce the screw mounts 9 in a vertebra by limiting relative movement between the screw mounts.

It is to be understood that while a certain form of the invention is illustrated, it is not to be limited to the specific form or arrangement herein described and shown. It will be apparent to those skilled in the art that various changes may be made without departing from the scope of the invention and the invention is not to be considered limited to what is shown and described in the specification and any drawings/figures included herein.

One skilled in the art will readily appreciate that the present invention is well adapted to carry out the objectives and obtain the ends and advantages mentioned, as well as those inherent therein. The embodiments, methods, procedures and techniques described herein are presently representative of the preferred embodiments, are intended to be exemplary and are not intended as limitations on the scope. Changes therein and other uses will occur to those skilled in the art which are encompassed within the spirit of the invention and are defined by the scope of the appended claims. Although the invention has been described in connection with specific preferred embodiments, it should be understood that the invention as claimed should not be unduly limited to such specific embodiments. Indeed, various modifications of the described modes for carrying out the invention which are obvious to those skilled in the art are intended to be within the scope of the following claims.

What is claimed is:

1. A method of performing spinal surgery, the method comprising:
    providing access to a posterior of the spine;
    securing a first rod between a first pair screw mounts;
    securing a second rod between a second pair of screw mounts, wherein the second rod is positioned on an opposite side of the spine as the first rod, and wherein the first rod and second rod are longitudinal with respect to the spine;
    connecting a first hook to the first rod in a position between the first pair of screw mounts;
    connecting a second hook to the second rod in a position between the second pair of screw mounts, wherein a flexible connector extends between the first hook and the second hook and transverse with respect to the first rod and the second rod;
    applying tension to the flexible connector; and
    mounting a rigid connector to the first hook and the second hook to fix the spacing between the first and second hooks, wherein the rigid connector has an upper surface facing away from the first and second hooks, a lower surface facing toward the first and second hooks, a first side surface connecting the upper and lower surfaces, and a second side surface connecting the upper and lower surfaces, wherein at least one of the first or second side surfaces of the rigid connector includes a channel to receive at least a portion of the flexible connector to limit vertical movement of the flexible connector, and wherein the flexible connector is positioned between the upper surface and the lower surface of the rigid connector.

2. The method of claim 1, wherein the flexible connector comprises a metal cable.

3. The method of claim 1, wherein the first hook comprises a throat for receiving the first rod therein.

4. The method of claim 3, wherein the throat is defined by a shank, a bight, a leg and a latch.

5. The method of claim 1, wherein the first hook includes one or more rounded edges.

6. The method of claim 1, wherein the first hook comprises a latch having an inclined surface.

7. The method of claim 1, wherein the rigid connector comprises a first end portion and a second end portion, wherein each of the first end portion and the second end portion of the rigid connector includes a pair of fingers with the channel formed therebetween.

8. The method of claim 7, wherein each of the pair of fingers is configured to receive a shank of either the first hook or the second hook.

9. The method of claim 1, wherein the rigid connector comprises an open sided groove.

10. The method of claim 9, wherein the open sided groove is configured to receive the flexible connector therein.

11. A method of performing spinal surgery, the method comprising:
    providing access to the spine;
    securing a first rod between a first pair screw mounts;
    securing a second rod between a second pair of screw mounts, wherein the second rod is positioned on an opposite side of the spine as the first rod, and wherein the first rod and second rod are longitudinal with respect to the spine;
    connecting a first hook having a first throat to the first rod;
    connecting a second hook having a second throat to the second rod, wherein a flexible connector extends between the first hook and the second hook;
    applying tension to the flexible connector with a tensioning tool having a handle and a shaft for applying tension to the flexible connector; and
    mounting a non-resilient connector to the first hook and the second hook to fix the spacing between the first and second hooks.

12. The method of claim 11, wherein the flexible connector comprises a metal cable.

13. The method of claim 11, wherein the non-resilient connector includes a channel to receive at least a portion of the flexible connector therein.

14. The method of claim 11, wherein the throat is defined by a shank, a bight, a leg and a latch.

15. The method of claim 11, wherein the first hook includes one or more rounded edges.

16. The method of claim 11, wherein the first hook comprises a latch having an inclined surface.

17. The method of claim 11, wherein the non-resilient connector comprises a first end portion and a second end portion, wherein each of the first end portion and the second end portion includes a pair of fingers with a channel formed therebetween.

18. The method of claim 17, wherein each of the pair of fingers is configured to receive a shank of either the first hook or the second hook.

19. The method of claim 11, wherein the non-resilient connector comprises an open sided groove.

20. The method of claim 19, wherein the open sided groove is configured to receive the flexible connector therein.

\* \* \* \* \*